(12) United States Patent
Garbini et al.

(10) Patent No.: US 7,694,809 B2
(45) Date of Patent: Apr. 13, 2010

(54) REMOTE ENABLING/DISABLING OF A LIMITED-USE MEDICAL DEVICE

(75) Inventors: Lex J. Garbini, El Granada, CA (US); Douglas B. Dull, San Jose, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 569 days.

(21) Appl. No.: 11/295,792

(22) Filed: Dec. 6, 2005

(65) Prior Publication Data

US 2007/0129684 A1  Jun. 7, 2007

(51) Int. Cl.
*B65D 83/10* (2006.01)

(52) U.S. Cl. .................................... 206/364

(58) Field of Classification Search .............. 206/363, 206/364, 367, 438, 439
See application file for complete search history.

(56) References Cited

U.S. PATENT DOCUMENTS

| | | | |
|---|---|---|---|
| 5,400,267 A | | 3/1995 | Denen et al. |
| 5,873,814 A | * | 2/1999 | Adair .......................... 600/109 |
| 6,270,460 B1 | | 8/2001 | McCartan et al. |
| 6,520,326 B2 | * | 2/2003 | McIvor et al. ................ 206/305 |
| 7,108,711 B2 | * | 9/2006 | Vogel et al. ..................... 607/1 |
| 7,312,984 B2 | * | 12/2007 | Richardson et al. ..... 361/679.41 |
| 7,362,228 B2 | * | 4/2008 | Nycz et al. ................ 340/572.1 |
| 2004/0243162 A1 | * | 12/2004 | Wulfman et al. ............. 606/167 |
| 2005/0004559 A1 | | 1/2005 | Quick et al. |
| 2005/0043594 A1 | | 2/2005 | Dinsmoor et al. |
| 2005/0109648 A1 | * | 5/2005 | Kerzman et al. ............ 206/364 |
| 2005/0109829 A1 | | 5/2005 | Postma |
| 2006/0163097 A1 | * | 7/2006 | Murray et al. ............... 206/364 |

* cited by examiner

*Primary Examiner*—Jacob K Ackun, Jr.

(57) ABSTRACT

A remotely controlled medical instrument enhances safety and reliability. The medical instrument may be remotely enabled (unlocked) or disabled (locked). The medical instrument may be intended for limited-use. The medical instrument may be enclosed within a medical packaging and subsequently sterilized. After the medical instrument is determined to meet desired specifications, a remote control device may remotely enable the medical instrument. The remote control device may remotely enable the medical instrument through the sterile barrier and without making direct contact with the medical instrument such that the medical instrument remains sterilized. The non-contact interaction between the medical instrument and the remote control device may be via infrared, electromagnetic, magnetic, or other non-contact communication techniques. The remote control device may remotely disable the medical instrument. The remote controller may transmit a key code to prevent the inadvertent and/or unauthorized enabling or disabling of the limited-use medical device.

11 Claims, 4 Drawing Sheets

REMOTE ENABLING/DISABLING OF A LIMITED-USE MEDICAL DEVICE

BACKGROUND

The present embodiments relate generally to medical devices. In particular, the present embodiments relate to limited-use and/or sterilized medical instruments.

Conventional medical systems may (1) provide little or no control over limited-use medical devices, (2) involve non-reversible enabling methods, or (3) involve a physical connection directly to the limited-use medical device. For instance, typical medical devices may be intended for only a limited number of uses. Allowing such devices to be used an unlimited number of times may adversely affect safety, efficacy, and reliability.

Conventional medical devices also may use locking systems that are irreversible. For example, some medical devices employ a series of fuses to establish an upper limit on the number of device reuses. However, non-reversible enabling methods may result in fully functional devices being discarded prematurely.

BRIEF SUMMARY

By way of introduction, the embodiments described below include methods, processes, apparatuses, instructions, or systems for remotely controlling sterilized medical instruments. Medical instruments may be effectively enclosed within a sterile barrier. The sterile barrier may be medical packaging manufactured from a permeable material that permits the passage of a sterilization agent while preventing the passage of unwanted organisms. After enclosing the medical instrument within the sterile barrier, a sterilization procedure may sterilize the medical instrument. Subsequently, the medical instrument may be remotely enabled and/or disabled via interaction or communication between the medical instrument and a remote control device through the sterile barrier, such that the medical instrument remains sterilized.

In a first aspect, a medical device includes a medical instrument and a sterile packaging surrounding the medical instrument. The medical instrument is operable to be remotely controlled without breaching the sterile barrier.

In a second aspect, a method remotely controls a medical instrument. The method includes effectively enclosing a medical instrument within a medical packaging and remotely enabling the medical instrument through the medical packaging.

In a third aspect, a method includes sterilizing a medical instrument and remotely controlling the medical instrument such that the medical instrument remains sterilized after being remotely controlled.

In a fourth aspect, a computer-readable medium having instructions executable on a computer stored thereon is described. The instructions include remotely transmitting to a sterilized medical instrument having a sterile barrier. The sterilized medical instrument is responsive to the transmission without breaching the sterile barrier such that the sterilized medical instrument remains sterilized after receiving the transmission.

The present invention is defined by the following claims. Nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The present invention will become more fully understood from the detailed description given herein and the accompanying drawings which are given by way of illustration only, and are not limitative of the present invention, and wherein.

DETAILED DESCRIPTION OF THE PREFERRED EMBODIMENTS

A medical instrument may be remotely controlled. For instance, the medical instrument may be remotely enabled (unlocked) and/or remotely disabled (locked). The medical instrument may be effectively enclosed within a medical packaging. The medical packaging may be manufactured from a permeable material. During a sterilization procedure, the medical packaging may permit the passage of a sterilization agent through the medical packaging that sterilizes the medical instrument. After which, the medical packaging may act as a sterile barrier that maintains the medical instrument sterilized until use.

If the medical instrument has been manufactured and sterilized to desired specifications, the medical instrument may be remotely enabled without breaching the sterile barrier to become operational. The medical instrument may be remotely disabled if specifications have not been met initially or are no longer satisfied after the passage of a given period of time. Additionally, the medical instrument may be remotely re-enabled after being either inadvertently or intentionally disabled without breaching the sterile barrier, such as if technical specifications are determined to still be within acceptable limits. After initial enablement, the medical instrument may be operational for a predetermined limited number of times, such as a single use or an amount of time. The enabling and/or disabling of the medical instrument may be dependent upon the medical instrument receiving a key or other identification code sent from a remote control device. The remote control device may interact with the medical instrument via infrared, electromagnetic, magnetic, or other communication techniques.

I. Exemplary Medical Instrument

Figure 1:
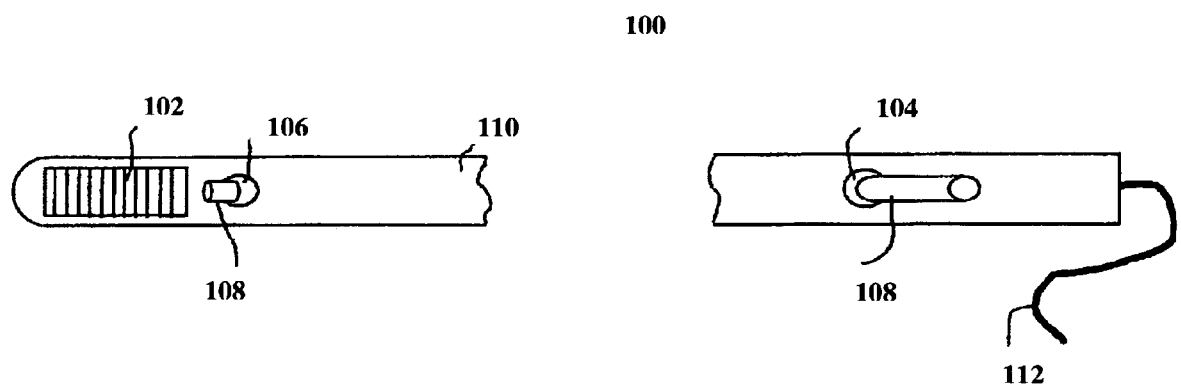
FIG. 1 illustrates an exemplary medical instrument.

An analog and/or digital circuit may receive and process remotely transmitted signals. The example of FIG. 1 shows a catheter tip based ultrasound probe 100 comprising a micro-mechanical ultrasound array 102, one or more working ports 104, 106, an insertable device 108, a housing 110, and a cable 112 which connects the array 102 to an ultrasound system (not shown). The catheter tip/probe may include additional, fewer, or alternative components. Various medical instruments may include micro-machined or other components for which the remote control thereof may be feasible and/or desirable. For example, FIG. 1 illustrates an exemplary medical instrument as disclosed by U.S. Pat. No. 6,645,145, which is incorporated herein in its entirety by reference.

The housing 110 may be constructed of a molded polymeric material, such as Pebax, or other suitable material. The housing 110 may be dimensioned for use within a patient, such as being dimensioned for insertion into a lumen, the heart, other portion of the cardiac system, or other internal part of a patient. The housing 110 may enclose the array 102 and the connector 112. In other embodiments, the housing 110 is shaped and sized for use outside of the patient.

The array 102 may support multiple imaging modalities, such as B-mode imaging, Doppler imaging, tissue harmonic imaging, contrast agent harmonic imaging, or other types of imaging. The catheter based ultrasound probe 100 may include other micro-mechanical components such as switches, relays, and/or inductors. These components may manipulate the frequency/acoustic spectra of the individual elements of the array and/or be used for signal amplification or attenuation.

In one embodiment, the imaging catheter is utilized in conjunction with an external ultrasound imaging array. The external array may be outside of the patient's body and used to image the position of a catheter within the body by sensing ultrasonic transmissions of the catheter probe.

In another embodiment, the probe housing 110 provides one or more working ports 104, 106 through which insertable devices 108 may be inserted. The working ports 104, 106 may be used by instruments, such as endoscopes and laparoscopes, which have tubular holes in which microsurgical instruments may be inserted for taking biopsies, making incisions, and/or grabbing items of interest. One port 106 may be located near the array 102 and the other port 104 near a user handle. This arrangement may facilitate the insertion of a device 108 proximate to the area of the patient being imaged. Such devices 108 may include tissue ablation devices, tissue mapping devices, biopsy devices, radiation therapy devices, implant delivery devices, and/or drug or contrast agent devices.

In another embodiment, the probe 100 may provide capabilities other than imaging capabilities. For instance, the probe 100 may be an ultrasound therapy device operative to deliver therapeutic ultrasound to the imaged portion of the subject. The probe may contain integrated tissue ablation electrodes or biopsy devices used to ablate or biopsy tissue in the imaged portion of the subject. The probe may sense position, measure local electric fields, and/or be operative to perform electrical surface mapping. Other types of medical instruments may be used, including intracardiac echocardiography (ICE) probes, transesophageal echocardiography (TEE) probes, and medical instruments directed toward the applications discussed below.

In another embodiment, the probe may be an ultrasound probe for diagnostic medical ultrasound imaging that includes an ultrasound transducer and a circuit having a plurality of states to limit the use of the ultrasound probe. The probe may employ a series of electrically programmable fuses to limit the number of usages of the probe, such as disclosed by U.S. Pat. No. 6,270,460, which is incorporated herein in its entirety by reference.

II. Exemplary Method of Remote Control

Figure 2:
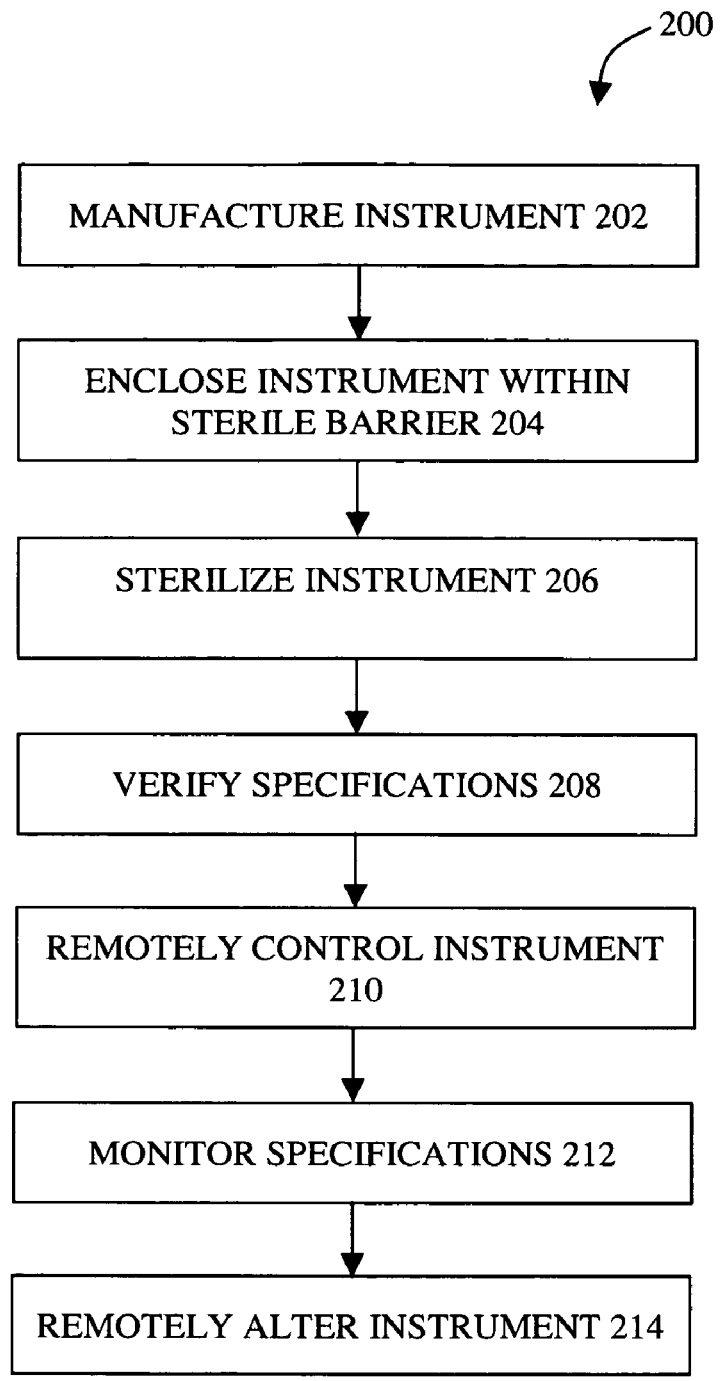
FIG. 2 illustrates a flow chart of an exemplary method for remotely controlling a medical instrument.

FIG. 2 illustrates an exemplary method 200 of remotely controlling a medical instrument. The method 200 may include manufacturing the medical instrument 202, enclosing the medical instrument within a sterile barrier 204, sterilizing the medical instrument 206, verifying the specifications of the medical instrument 208, remotely controlling the medical instrument 210, monitoring the specifications of the medical instrument 212, and remotely adjusting or altering the medical instrument 214. The method may include additional, fewer, or alternative actions.

The method 200 may include manufacturing a medical instrument 202 using any conventional manufacturing method known in the art. The medical instrument manufactured may be intended for limited-use. The limited-use medical instrument may be capable of permitting the remote control of the enabling (unlocking) and/or disabling (locking) of the medical instrument. Locking the limited-use medical instrument may be critical to maintaining safety, efficacy, and reliability. Remotely controlling the locking and unlocking of the limited-use medical instrument may provide the manufacturer with enhanced control over the use of the medical instrument.

In one embodiment, the medical instrument manufactured may be similar to the device shown in FIG. 1 or the other medical devices and probes discussed above. However, more generally, the medical instrument may be directed to any number of various medical applications. For instance, transducer probes and/or other medical instruments manufactured to include a circuit or micro-machined components may be directed toward intracardiac, endoluminal, endocavity, and other medical applications internal to a patient. The medical application may utilize the size and image processing capabilities offered by micro-machined based or piezoelectric probes. The instrument may be for non-imaging applications.

Alternatively, the probes and/or medical instruments may be used during imaging processes that produce patient images or scans of internal regions of interest. The imaging processes may include radiography, angioplasty, computerized tomography, ultrasound and magnetic resonance imaging (MRI) processes. Additional types of imaging processes that may employ the probe and/or medical instrument may include perfusion and diffusion weighted MRI, cardiac computed tomography, computerized axial tomographic scan, electron-beam computed tomography, radionuclide imaging, radionuclide angiography, single photon emission computed tomography (SPECT), cardiac positron emission tomography (PET), digital cardiac angiography (DSA), digital subtraction angiography (DSA), and other imaging processes.

Figure 3:
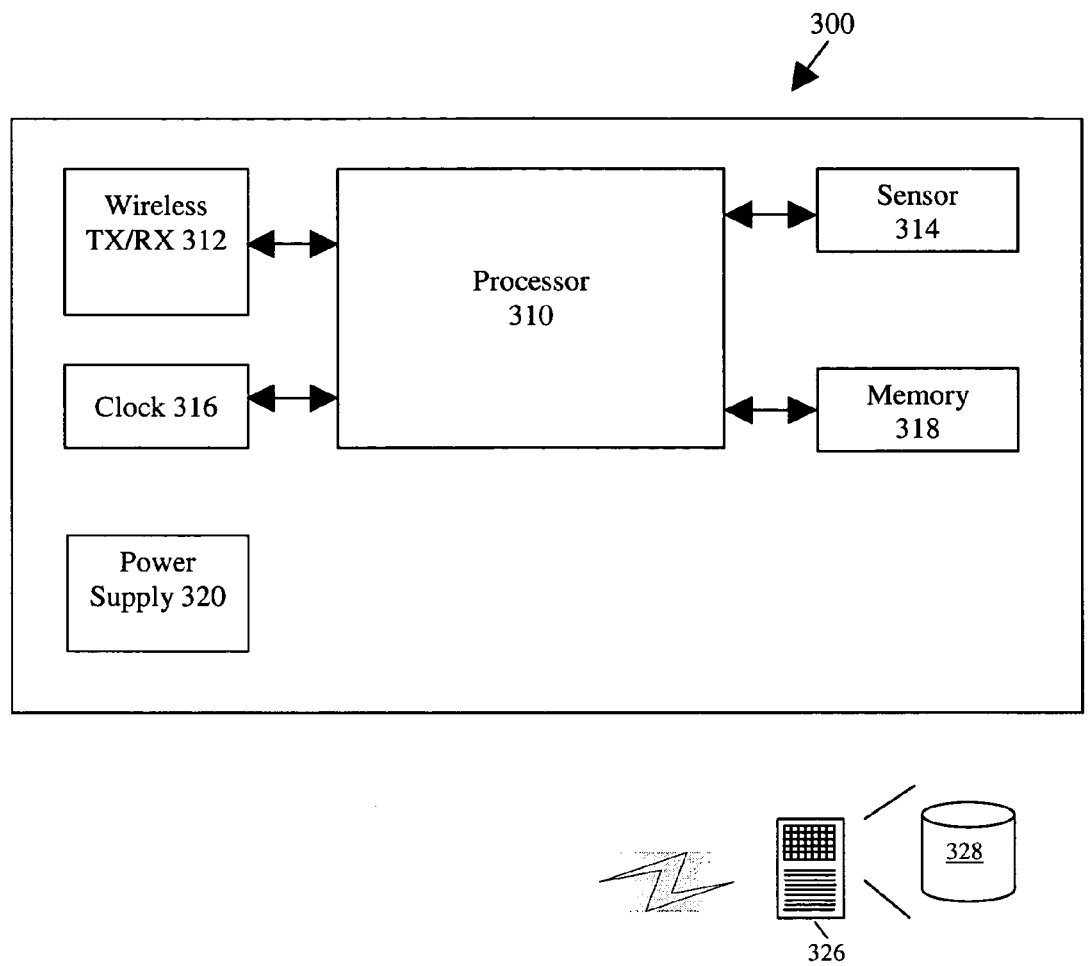
FIG. 3 illustrates an exemplary control circuit associated with a medical instrument.

The medical instrument may include control circuitry. FIG. 3 illustrates exemplary control circuitry 300 for the medical instrument. The control circuitry 300 may include a processor 310, a wireless radio frequency transmitter and/or receiver 312, a sensor 314, a clock 316, a memory 318, and a power supply 320. The control circuitry 300 may include other combinations employing additional, fewer, or different components, such as no integrated power supply 320.

The processor 310 may be capable of processing data and/or controlling operation of the medical instrument 300. The processor 310 may be a general processor, digital signal processor, application-specific integrated circuit (ASIC), field programmable gate array, analog circuit, digital circuit, network of processors, programmable logic controller, fuse, micro-electromechanical device, or other processing device. The processor 310 may have an internal memory.

The control circuitry 300 may have a memory unit 318 external to the processor 310. The memory unit 318 may store data and instructions for the operation and control of the medical instrument. Additional or alternate types of data also may be stored in the memory unit 318.

A program may reside on the internal memory or the memory unit 318 and include one or more sequences of executable code or coded instructions that are executed by the processor 310. The program may be loaded into the internal memory or memory unit 318 from a storage device. The processor 310 may execute one or more sequences of instructions of the program to process data. Data may be input to the data processor 310 with a data input device, such as a remote controller, and/or received from a network. The program and other data may be stored on or read from machine-readable medium, including secondary storage devices such as hard disks, floppy disks, CD-ROMS, and DVDs; electromagnetic signals; or other forms of machine readable medium, either currently known or later developed.

In one embodiment, the coded instructions stored on the computer-readable medium may include instructions for remotely controlling a sterilized medical instrument having a sterile barrier such that the sterilized medical instrument may be remotely controlled without breaching the sterile barrier, which maintains the medical instrument sterilized after being remotely controlled. The instructions may include verifying an identification code sent from a remote control device. The instructions may include enabling and/or disabling a medical instrument effectively enclosed in a medical packaging and/or other sterile barrier. The instructions may include re-enabling the sterilized medical instrument after the sterilized medical instrument has become either intentionally or inadvertently disabled. Additional, fewer, and alternative instructions may be used.

The processor 310 is capable of directing the transmission or reception of data by the wireless transmitter and/or receiver 312. The processor 310 is capable of monitoring time via the clock 316 and may perform certain functions based upon measured time periods. The processor 310 may perform certain functions based upon information received from the sensor 314, which may be an infrared component, magnetic field (i.e., inductive) component, electromagnetic component, or other sensor. The control circuitry 300 may have a power supply 320, such as a battery, solar cell, capacitor, or micro-electrical mechanical (MEMS) device that generates or receives transmitted energy.

As shown in FIG. 3, the control circuitry 300 may be operable to receive and transmit data from a remote controller 326. The remote controller 326 may be a handheld device or a workstation, such as discussed further below. The remote controller 326 may have either direct or indirect access to a database 328. The database 328 may contain data, such as technical specifications and limits, and instructions associated with the medical instrument.

After the medical instrument has been manufactured and all testing that may require direct contact with the instrument has been completed, the method 200 may include effectively enclosing, such as by wrapping or sealing, the medical instrument within a sterile barrier 204. The sterile barrier may be medical packaging. The medical packaging may be plastic, foil, film, sealing, medical-grade paper, or other types of medical packaging. For instance, the medical packaging may be manufactured from a permeable material that permits a sterilization agent to pass through the medical packaging but does not allow bacterial agents or other unwanted microorganisms to pass through and contaminate the medical instrument after sterilization.

Once the medical instrument is enclosed within the bacterial barrier, the method 200 may include sterilizing the medical instrument via a sterilization procedure 206. The sterilization procedure may involve the use of ethylene oxide (EtO), gamma, electron-beam, steam, and plasma/hydrogen peroxide sterilization agents. Other sterilization processes and agents may be used. Sterilization may occur before enclosing the instrument.

In one embodiment, the sterilization procedure may involve the use of ethylene oxide (EtO) gas. The EtO sterilization method may have four primary phases: (1) air removal, (2) steam injection, (3) EtO injection, and (4) gas purge. During the EtO sterilization method, the EtO may pass through the medical packaging and sterilize the medical instrument. Although sterilization gases such as EtO may penetrate and pass through the medical packaging, bacteria and other microorganisms may not. After evacuation of the gases, no new unwanted microorganisms are likely to gain access to the medical instrument, and the instrument may remain sterilized within the medical packaging.

The method 200 may include verifying technical specifications of the medical instrument after the packaging and sterilization processes have been completed 208. A technician may verify that aspects of manufacturing have been satisfactorily completed. Additionally, after the medical instrument is sterilized, the instrument may be quarantined for a specified time (for example to allow the EtO residuals to diffuse out of the packaging). The quarantine may be secured after the EtO diffusion time has passed and all other aspects of medical instrument quality have been verified, such as biological indicators.

The method 200 may include remotely controlling the medical instrument 218. For instance, a technician may remotely (e.g., through the packaging) enable and/or disable the medical instrument for use. Remote includes adjacent but separated or spaced away with or without separation by packaging. As a result of the non-contact enabling and/or disabling of the limited-use medical instrument, the seal of the instrument packaging does not need to be broken in order to control the instrument. In other words, the enabling and/or disabling may be accomplished through the sterile barrier and independent of direct physical contact between the medical instrument and a remote control device. Other controls than enabling or disabling may be provided, such as coding, electronically labeling (stored code), or programming.

Any method of non-contact communications between the limited-use medical device (lock) and the remote transmitter (key) may be employed. The list of methods includes, but is not limited to, infrared (I/R), electromagnetic (RF, microwave, etc.), and/or magnetic (inductive). Remote enablement of the medical device may ensure that the instrument is operationally enabled only after all of the required manufacturing processes have been completed. Additionally, remote enablement may increase the probability that the medical instrument is in excellent condition when it reaches the customer.

More specifically, the medical instrument may be coupled with a remote transmitter or remote control device. The remote control device may be the hand held remote controller or data processing system discussed herein. In one embodiment, the medical instrument may be inductively coupled with the remote control device, such as described in U.S. Pat. No. 4,725,839, which is incorporated herein in its entirety by reference. Other inductive coupling techniques known in the art may be employed.

In another embodiment, the medical instrument may be coupled via infrared interaction with the remote control device, such as described in U.S. Pat. No. 5,537,463, which is incorporated herein in its entirely by reference. Other techniques of infrared coupling known in the art may be used.

In another embodiment, the medical instrument may be electromagnetically coupled with the remote control device, such as described in U.S. Pat. Nos. 6,645,145 and 5,537,463, both of which are incorporated herein in their entirety by reference. Other methods of electromagnetic coupling known in the art may be used, such as radio frequency tag identification techniques.

Figure 4:
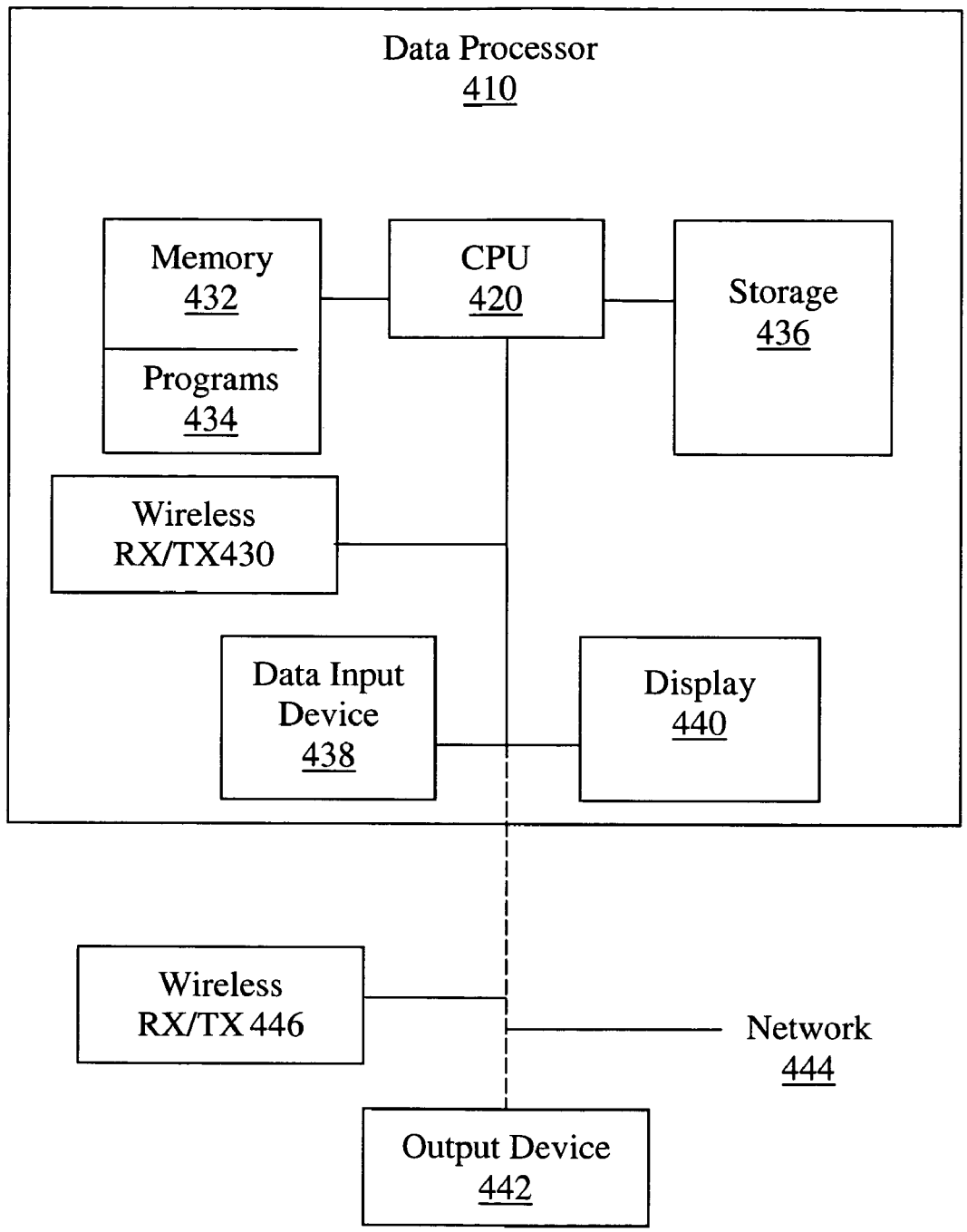
FIG. 4 illustrates an exemplary data processing system.

The method 200 may employ a data processing system and/or a hand held transmitter, such as shown in FIG. 3, to remotely control the medical instrument. FIG. 4 illustrates an exemplary data processor 410 configured or adapted to remotely control the medical instrument. The data processor 410 may include a central processing unit (CPU) 420, a wireless radio frequency transmitter and/or receiver 430, a memory 432, a storage device 436, a data input device 438, and a display 440. The processor 410 also may have an external output device 442, which may be a display, a monitor, a printer or a communications port. The processor may have additional, fewer, or alternate components.

The processor 410 may be a personal computer, work station, pictorial archival communication system (PACS) station, C-arm imaging system, x-ray system, ultrasound imaging system, other imaging system, or other medical system. The processor 410 may be interconnected to a network 444, such as an intranet, the Internet, or an intranet connected to the Internet or a wireless radio frequency transmitter and/or receiver 446. The processor 410 is provided for descriptive purposes and is not intended to limit the scope of the present system.

A program 434 may reside on the memory 432 and include one or more sequences of executable code or coded instructions that are executed by the CPU 420. The program 434 may be loaded into the memory 432 from the storage device 436. The CPU 420 may execute one or more sequences of instructions of the program 434 to process data. Data and/or instructions may be input to the processor 410 with the data input device 438, transmitter and/or receiver 430, received from the network 444, and/or external transmitter and/or receiver 446. The program 434 may interface the data input device 438, transmitter and/or receiver 430, and/or the network 444 for the input of data. Data processed by the processor 410 may be provided as an output to the display 440, the external output device 442, the network 444, transmitter and/or receiver 430, external transmitter and/or receiver 446, and/or stored in a database. The program 434 and other data may be stored on or read from machine-readable medium, including RAM, cache, or secondary storage devices such as hard disks, floppy disks, CD-ROMs, and DVDs; electromagnetic signals; or alternate forms of machine readable medium, either currently known or later developed. In one embodiment, the coded instructions stored on the computer-readable medium may include similar or identical instructions as identified above with respect to FIG. 3 regarding the remote control of the medical instrument.

The processor 410 may run a software application or program 434 that performs a number of operations related to an imaging system. The processor 410 may access data stored on or read from machine-readable medium, including RAM, cache, or secondary storage devices such as hard disks, floppy disks, CD-ROMs, and DVDs; electromagnetic signals; or alternate forms of machine readable medium, either currently known or later developed.

The data processor 410 may wirelessly communicate with the medical instrument. In one embodiment, the external wireless radio frequency transmitter and/or receiver 446 is associated with or mounted on the medical instrument and the internal wireless radio frequency transmitter and/or receiver 430 is associated with the data processor 410. Alternatively, the remote controller of FIG. 3 may wirelessly communicate with the medical instrument. In another embodiment, the remote controller may be in wireless communication with the data processing system 400.

The method 200 may include monitoring the specifications of the one or more medical instruments 212. For instance, the shelf life of a batch of medical instruments may be extended through additional monitoring and data collection associated with the batch. As a result, after a limited-use medical instrument has been disabled as having exceeded an initial shelf life, the instrument may be deemed to still meet specifications due to a revised and more accurate shelf life. Alternatively, a medical device may be determined to have exceeded a shelf life or other specification.

Accordingly, the method 200 may include remotely altering the operational mode of the medical instrument 214. For instance, a technician may remotely re-enable the medical instrument without breaching the sterile barrier if the instrument still meets specifications. Alternatively, an enabled device may be disabled without breaking the sterile barrier if the shelf life or other specification has been exceeded.

Alternatively, after the limited-use instrument has been used for the intended purpose, the instrument may be submitted to a qualified technician to assess the instrument's, such as an echocardiography probe, functionality against established manufacturing specifications. The instrument may be repackaged and re-sterilized as required by the manufacturer's specifications. The qualified technician may use a remote transmitter or other device to reactivate the instrument.

The remote transmitter may be preprogrammed with an appropriate code or the code could be entered manually (to allow for periodic modification). A complex remote transmitter code may prevent inadvertent enabling and/or disabling of the medical instrument. Encapsulation of the receiver mechanism within the device control circuitry may prevent enabling and/or disabling by unauthorized persons.

In one embodiment, after the limited-use instrument has been used, the instrument will subsequently automatically become disabled. For instance, after being disconnected from a medical system, the instrument may countdown for a predetermined time. If the instrument is not reconnected prior to the completion the countdown, the device will be automatically disabled.

The remote control of the medical instrument may facilitate the highly controlled reuse of the medical instrument. For instance, after a limited-use medical instrument (for example a single-use device) has been used once, there is the possibility to clean, and re-sterilize the device for potential reuse. However, the quality of the used instrument may be degraded. A remotely enabled instrument allows the manufacturer to retain more control over the use of the medical instrument. For instance, the medical instrument may be remotely enabled only after a qualified technician has reviewed all of the appropriate results from various tests and process monitoring (including sterilization related processes). Encrypted signals may enable or disable the instrument to avoid unauthorized control.

Additionally, the remote control of sterilized medical instruments may facilitate enhanced control over quarantine populations of medical instruments. Occasionally, even the best-controlled manufacturing process may experience difficulties. The difficulties may result in a group of medical instruments being characterized as not-ready-for-shipment and withheld from shipment to a customer. For instance, a device performance test, representing a lot or batch of 100 catheters or other instruments, may have fallen below the lower control limit. As the lot is evaluated for acceptability, there may be a small risk that these quarantined catheters could be accidentally shipped. A remote enabling and/or disabling system allows the remote deactivation of any previously enabled catheters or other instruments inadvertently shipped or waiting for shipment. Accordingly, the remote control of medical instruments may prevent the unintentional use of any instrument not cleared for use.

The remote control of medical instruments may provide enhanced control over the use of the medical instruments. As discussed herein, the limited-use medical instruments may contain a receiver and a transmitter. The remote control device, such as a remote controller or data processing system, also may contain a receiver and a transmitter. The remote control device may send an enable and/or disable command to the medical instrument. The medical instrument may send an acknowledgement of the command back to the remote control device. The remote control device may query the current state or mode, such as being enabled or disabled or how many operational uses are left before automatic disablement, of the medical instrument.

The remote control of sterilized medical instruments provides a new business model to medical instrument manufacturers. A high-volume user may be fully or partially trained in the techniques required to properly reprocess a limited-use instrument. The high-volume user also may be trained in properly evaluating the suitability of the reprocessed instrument for reuse. After sufficient education and training, the opportunity may exist to sell medical instrument usages, rather than instruments. In one embodiment, the remote enabling controller or data processing system may contain a counter used to determine the number of instrument usages. Based upon the number of instrument usages, the customer may be billed accordingly. The counter and associated electronics may be contained within a remote controller, the instrument, or associated with the data processing system.

The various methods of non-contact communication may require differing levels of signal discrimination. The inductive communication method, which may be used over a short distance, such as a few inches, may only require close proximity between the limited-use medical instrument and the remote control device, such as a hand held remote controller, to effectively discriminate between different individual limited-use medical instruments. Signal discrimination may be needed to ensure that the correct medical instrument receives the intended remote command. Alternatively, the RF communication method may require the use of a distinct identification or key code that is associated with a specific limited-use medical instrument. The identification code may include the device model number and/or serial number.

The remote control of sterilized medical instruments may enhance the control of maintenance. As discussed herein, the medical instrument may be designed for many uses. However, the medical instrument may require routine or periodic maintenance to operate properly. The planning and performance of such periodic maintenance may be improved. A remote controller, data processing system, or other remote control device may be associated with the limited-use medical instrument. After the remote controller, instrument, data processing system, or other remote control device has counted down the allowed number of uses, the medical instrument may be identified and inspected by a qualified technician (such as at the manufacturer's facility) to determine if the proper maintenance has been performed. If the maintenance has been completed satisfactorily, the instrument and/or remote controller may be reset and the medical instrument, as the remote control device, may be returned to the user. The process describe above also may be appropriate for calibration control of medical instruments.

While the invention has been described above by reference to various embodiments, it should be understood that many changes and modifications can be made without departing from the scope of the invention. The description and illustrations are by way of example only. Many more embodiments and implementations are possible within the scope of this invention and will be apparent to those of ordinary skill in the art. The various embodiments are not limited to the described environments and have a wide variety of applications.

It is intended in the appended claims to cover all such changes and modifications which fall within the true spirit and scope of the invention. Therefore, the invention is not limited to the specific details, representative embodiments, and illustrated examples in this description. Accordingly, the invention is not to be restricted except in light as necessitated by the accompanying claims and their equivalents.

What is claimed is:

1. A medical device comprising:
   a catheter configurable to be used a limited number of times or limited amount of time; and
   a verified sterile barrier on the catheter, the sterile barrier being formed by packaging;
   the catheter operable to be wirelessly and remotely enabled to unlock the catheter in order to allow use of the catheter, the enablement being while still in the packaging and without breaching the sterile barrier, the catheter configured by the unlocking to allow the use for the limited number or amount, the use being for a medical application in a patient, the catheter configured to automatically lock after the number of times or the limited amount of time, the lock preventing subsequent use of the catheter for the medical application in the patient.

2. The device of claim 1, wherein the catheter is operable to be remotely disabled without breaching the sterile barrier.

3. The device of claim 1, wherein the packaging is manufactured from a permeable material that permits passage of a sterilization agent.

4. The device of claim 3, wherein the catheter is sterilized via an ethylene oxide sterilization procedure after the catheter is effectively enclosed within the sterile barrier.

5. The device of claim 1, wherein the catheter is remotely controlled via infrared interaction between the catheter and a remote control device.

6. The device of claim 1, wherein the catheter is remotely controlled via electromagnetic interaction between the catheter and a remote control device.

7. The device of claim 1, wherein the catheter is remotely controlled via magnetic interaction between the catheter and a remote control device.

8. The device of claim 1, wherein the catheter is remotely enabled after receiving an identification code transmitted from a remote control device.

9. The device of claim 1 wherein the catheter is a used catheter, which has been disabled, and wherein the packaging comprises repackaging.

10. The device of claim 1 wherein the catheter is an imaging catheter and the use is for imaging while connected with an imaging system.

11. A medical device comprising:
    a medical instrument configurable to be used a limited number of times or limited amount of time; and
    medical packaging forming a verified sterile barrier that encloses the medical instrument;
    the medical instrument configured to be remotely unlocked prior to use in order to allow use of the medical instrument, the unlocking being while still in the packaging, and without breaching the sterile barrier, the medical instrument configured by the unlocking to allow the use for the limited number or amount, the use being for a medical application in a patient, the medical instrument configured to automatically lock after the number of times or the limited amount of time, the lock preventing subsequent use of the medical instrument for the medical application in the patient.

* * * * *